United States Patent
Lord et al.

(10) Patent No.: US 9,743,890 B2
(45) Date of Patent: Aug. 29, 2017

(54) SYSTEM AND METHOD FOR PROVIDING FAMILY MODE FOR MONITORING DEVICES

(75) Inventors: William Palmer Lord, Fishkill, NY (US); Cornelis Conradus Adrianus Maria Van Zon, Fishkill, NY (US); Steffen Clarence Pauws, Eindhoven (NL); Juergen Te Vrugt, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 429 days.

(21) Appl. No.: 14/006,690

(22) PCT Filed: Mar. 22, 2012

(86) PCT No.: PCT/IB2012/051362
§ 371 (c)(1),
(2), (4) Date: Sep. 23, 2013

(87) PCT Pub. No.: WO2012/131546
PCT Pub. Date: Oct. 4, 2012

(65) Prior Publication Data
US 2014/0018650 A1 Jan. 16, 2014

Related U.S. Application Data

(60) Provisional application No. 61/468,086, filed on Mar. 28, 2011.

(51) Int. Cl.
*A61B 5/00* (2006.01)
*A61B 5/021* (2006.01)
(Continued)

(52) U.S. Cl.
CPC ............ *A61B 5/742* (2013.01); *A61B 5/0002* (2013.01); *A61B 5/021* (2013.01); *A61B 5/024* (2013.01);
(Continued)

(58) Field of Classification Search
CPC ..... G06Q 50/24; G06F 19/327; G06F 19/322; G06F 19/3406; G06F 19/3418;
(Continued)

(56) References Cited

U.S. PATENT DOCUMENTS

2007/0039017 A1* 2/2007 Plocher ............................ 725/9
2007/0225575 A1   9/2007 Kilborn et al.
(Continued)

FOREIGN PATENT DOCUMENTS

| JP | 2003036312 A | 2/2003 |
|---|---|---|
| WO | 0130231 A2 | 5/2001 |
| WO | 2010007589 A1 | 1/2010 |

*Primary Examiner* — Gary Jackson
*Assistant Examiner* — Scott T Luan

(57) ABSTRACT

A device having a sensor detecting patient physiological data, a detection element detecting whether a medical professional is present in a patient's room and a display. If a medical professional is present in the patient's room, the display displays a first display mode, the first display mode including the patient physiological data. If a medical professional is not present in the patient's room, the display displays a second display mode, the second display mode being adapted for viewing by lay viewers.

16 Claims, 2 Drawing Sheets

(51) Int. Cl.
*A61B 5/024* (2006.01)
*A61B 5/1455* (2006.01)
*A61B 5/0402* (2006.01)
*A61B 5/08* (2006.01)
*G06F 19/00* (2011.01)

(52) U.S. Cl.
CPC .............. *A61B 5/0402* (2013.01); *A61B 5/08* (2013.01); *A61B 5/14551* (2013.01); *A61B 5/746* (2013.01); *G06F 19/3406* (2013.01); *G06F 19/3418* (2013.01)

(58) Field of Classification Search
CPC ......... A61B 5/742; A61B 5/024; A61B 5/746; A61B 5/0002; A61B 5/021; A61B 5/0402; A61B 5/08; A61B 5/14551; G08B 21/22; G08B 21/182
See application file for complete search history.

(56) References Cited

U.S. PATENT DOCUMENTS

| 2010/0127866 A1* | 5/2010 | Klein .................... A61B 5/1113 340/541 |
| 2011/0001605 A1* | 1/2011 | Kiani et al. ..................... 340/5.6 |
| 2011/0166871 A1* | 7/2011 | Ryan et al. ........................ 705/2 |
| 2011/0202371 A1* | 8/2011 | Darguesse et al. ................ 705/3 |

* cited by examiner

SYSTEM AND METHOD FOR PROVIDING FAMILY MODE FOR MONITORING DEVICES

This application is a national stage application under 35 U.S.C. §371 of International Application No. PCT/IB2012/051362 filed on Mar. 22, 2012 and published in the English language on Oct. 4, 2012 as International Publication No. WO/2012/131546, which claims priority to U.S. Application No. 61/468,086 filed on Mar. 28, 2011, the entire disclosures of which are incorporated herein by reference.

BACKGROUND

Patient monitoring devices measure and display important physiological data which may include electrocardiogram (ECG) data, respiratory rate, heart rate, oxygen saturation ($SO_pO_2$), blood pressure, etc. Measured values are typically displayed both in the patient's room and at a central monitoring station, and any alerts generated also typically occur both in the patient's room and at a central monitoring station. However, displayed information and alerts are typically not understood, or even misunderstood, by people without medical training, which may typically include the patient and any family members in the patient's room.

SUMMARY OF THE INVENTION

A device having a sensor detecting patient physiological data, a detection element detecting whether a medical professional is present in a patient's room and a display. If a medical professional is present in the patient's room, the display displays a first display mode, the first display mode including the patient physiological data. If a medical professional is not present in the patient's room, the display displays a second display mode, the second display mode being adapted for viewing by lay viewers.

A non-transitory computer-readable storage medium storing a set of instructions executable by a processor. The set of instructions being operable to receive patient physiological data and receive an indication indicating whether a medical professional is present in a patient's room. The set of instructions being further operable to display, on a display of a patient monitoring device, a first display mode, if a medical professional is present in the patient's room, the first display mode including the patient physiological data and display, on the display of the patient monitoring device, a second display mode, if a medical professional is not present in the patient's room, the second display mode being adapted for viewing by lay viewers.

DETAILED DESCRIPTION

Figure 1:
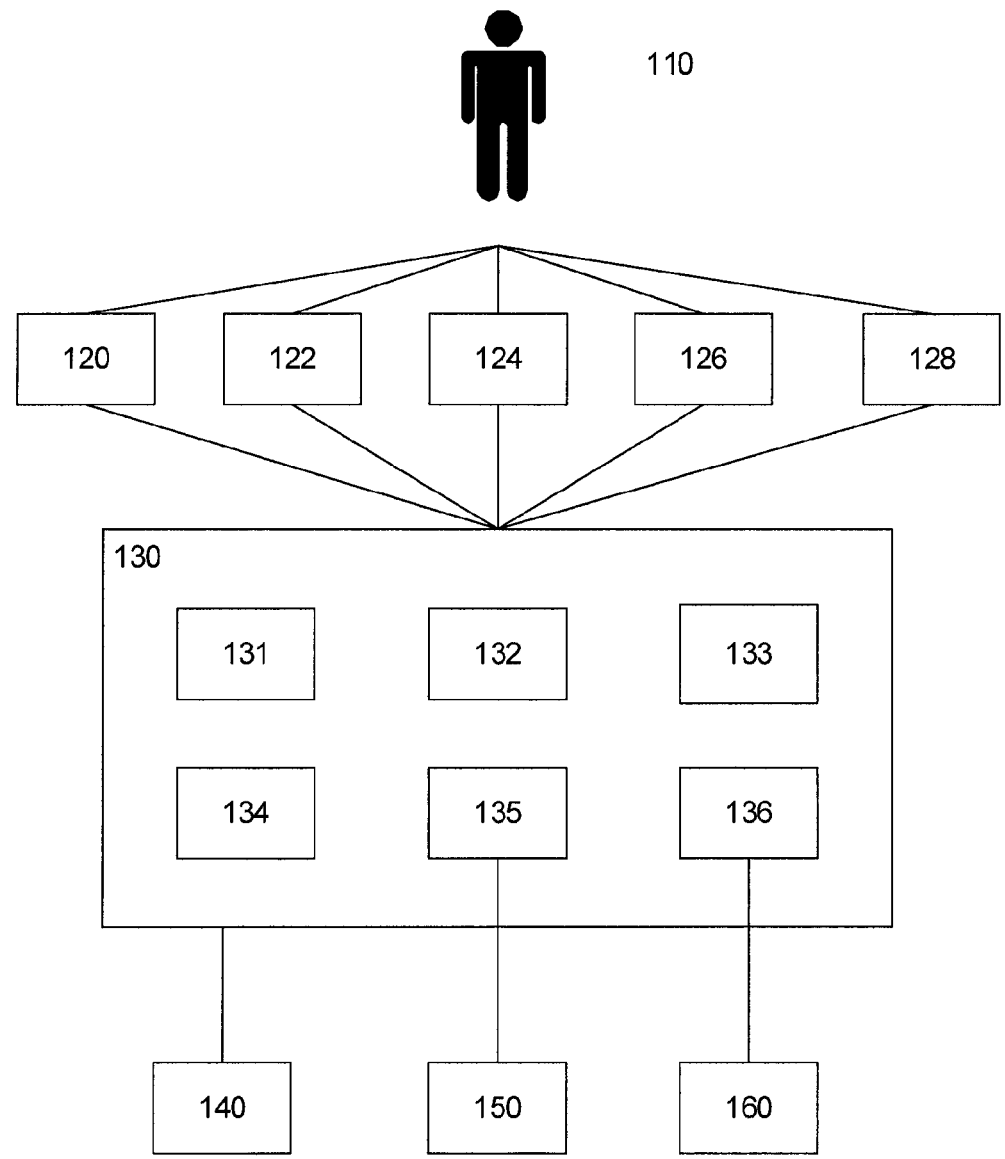
FIG. 1 illustrates a schematic view of an exemplary system for providing a family mode for patient monitoring devices.

The exemplary embodiments may be further understood with reference to the following description and the appended drawings, wherein like elements are referred to with the same reference numerals. The exemplary embodiments describe systems and methods by which family mode functionality may be provided using patient monitoring devices.

Patient monitoring devices measure and display important physiological data which may include electrocardiogram ECG data, respiratory rate, heart rate, $SO_pO_2$, blood pressure, etc. Measured values are typically displayed both in the patient's room and at a central monitoring station (e.g., a nurse's station). The measured physiological data may be associated with alarms to indicate to healthcare providers that attention to the patient (or to the patient's equipment) may be required. These alarms typically include an audible component and a visual component, and also typically occur both in the patient's room and at a central monitoring station.

However, information displayed by patient monitoring devices, and alarms generated by such devices, is typically not understood by people without medical training; this is typically the case both for the patient and any of the patient's family members or friends observing the monitoring devices. The information may even be misunderstood, resulting in the undertaking of inappropriate courses of action on the basis of the misunderstanding. Depending on which unit of a hospital or outpatient clinic a patient is being monitored in, the amount of time a healthcare professional is in the patient's room and able to see the in-room patient monitor is minimal; typically, this period of time may be less than one hour per day. This amount of time is even less when patient monitoring devices are used in the patient's home to support self-care and independent living. The exemplary embodiments present systems and methods for implementing a "family mode" or "patient mode" for such monitoring devices in order to provide to patients and their families information that is appropriate for those without medical training, and to avoid instances in which inappropriate action is taken due to misunderstanding of physiological data or alarms generated on the basis of such data.

FIG. 1 provides a schematic illustration of an exemplary system 100 for providing a patient monitoring device including family mode. The system 100 may be disposed, for example, in a hospital room, in a patient room in a rehabilitation center, etc. Similar systems may also be adapted for in-home monitoring of patients who are recovering from surgery, suffering from chronic conditions, etc. A patient 110 is monitored by a plurality of monitoring elements 120, 122, 124, 126 and 128, each of which monitors a particular type of physiological data of the patient 100. The monitoring element 120 is a set of ECG electrodes for measuring ECG data of the patient 100. The monitoring element 122 is a respiratory detection element for measuring the rate of respiration of the patient 100. The monitoring element 124 is a heart monitoring element for monitoring the heart rate of the patient 100. The monitoring element 126 is a pulse oximeter device for measuring the oxygen saturation of the patient 100. The monitoring element 128 is a blood pressure cuff for measuring the blood pressure of the patient 100. However, those of skill in the art will understand that the monitoring elements described above are only exemplary, and that in other systems different numbers of monitoring elements may be present, different data may be measured by the monitoring elements, and/or the types of data described above may be measured using different specific mechanisms, without departing from the broader principles described herein.

The monitoring elements 120, 122, 124, 126 and 128 are connected to a patient monitoring device 130 by any type of connection that is appropriate to the nature of each monitoring element (e.g., electrical wire, pneumatic tube for carrying pressure measurements, etc.). The patient monitoring device includes a processor 131 for processing data received from the monitoring elements 120, 122, 124, 126 and 128; a memory 132 for storing programs to be used by the processor 131 for data processing, for archiving processed data to be used for providing historical results regarding the patient 100, and for storing various other data as will be described herein; a display 133 (e.g., an LCD display, an LED display, or any other type of display) for displaying patient data and other data as will be described herein; a user interface 134 (e.g., a keyboard, a touchscreen, etc.) for receiving user input; a physiological data interface 135 for carrying measured patient physiological data to other locations (e.g., a central monitoring location 150, a remote storage, etc.); and a network data interface 136 for carrying other types of data to and from the patient monitoring device 130 and one or more remote data storage locations (e.g., a central hospital information database 160), as will be described in further detail below.

The system 100 also includes a medical professional detection element 140, which detects the presence of a medical professional (e.g., doctor, nurse practitioner, etc.) in the patient's room. In one embodiment, detection is accomplished automatically, by using active or passive badge technology (e.g., RFID technology, etc.) to detect a badge worn by a medical professional in the patient's room. In such an embodiment, the medical professional detection element 140 is a detector for detecting the presence of a badge using methods that are known in the art. The badge may be, for example, an identification badge worn by medical professionals for other purposes (e.g., security, access to restricted areas, access to parking, etc.). In one embodiment, the medical professional detection element 140 may be an integrated component of the patient monitoring device 130; in another, it may be an element of a general purpose sensing system in the room, or in the hospital as a whole, and may be linked to the patient monitoring device 130.

In another embodiment, the medical professional detection element 140 is a manual detection mechanism, such as a switch on the patient monitoring device 130 that is operative to toggle between different modes of the patient monitoring device 130 as will be described in further detail below. In such an embodiment, the switch may be coupled with a security mechanism (e.g., a keypad for entering a PIN code) in order to insure that only medical professionals are able to toggle the mode of the patient monitoring device 130. In another embodiment, the medical professional detection element 140 is a voice activation mechanism, such as a microphone coupled to a signal processing apparatus (e.g., a software program stored in the memory 132 and executed by the processor 131) for using voice recognition or voice understanding technologies to prompt a switch between different modes, as will be described in further detail below. In one such embodiment, all voices in the room are recorded, and a mode switch is prompted whenever the medical professional detection element 140 detects that one of the voices matches stored voice data (e.g., stored in the memory 132) for a medical professional; in another such embodiment, when a specific command (e.g., "switch mode") is spoken, the medical professional detection element 140 recognizes the spoken command using voice understanding technology, determines whether the command was spoken by a medical professional as described above, and, if so, switches the mode.

In another embodiment, the medical professional detection element 140 receives biometric input to recognize the presence of a medical professional. Biometric input may include fingerprint recognition (e.g., using a fingerprint detector to recognize a fingerprint swipe by a medical professional), facial recognition (e.g., using a video camera in the room to recognize the face of a medical professional), or other types of biometric data that can be used to identify an individual as a medical professional. In another embodiment, the medical professional detection element 140 may recognize an identification that is scanned by the medical professional, such as a bar code, magnetic strip, or other identifier present in an identification badge worn or carried by the medical professional.

Figure 2:
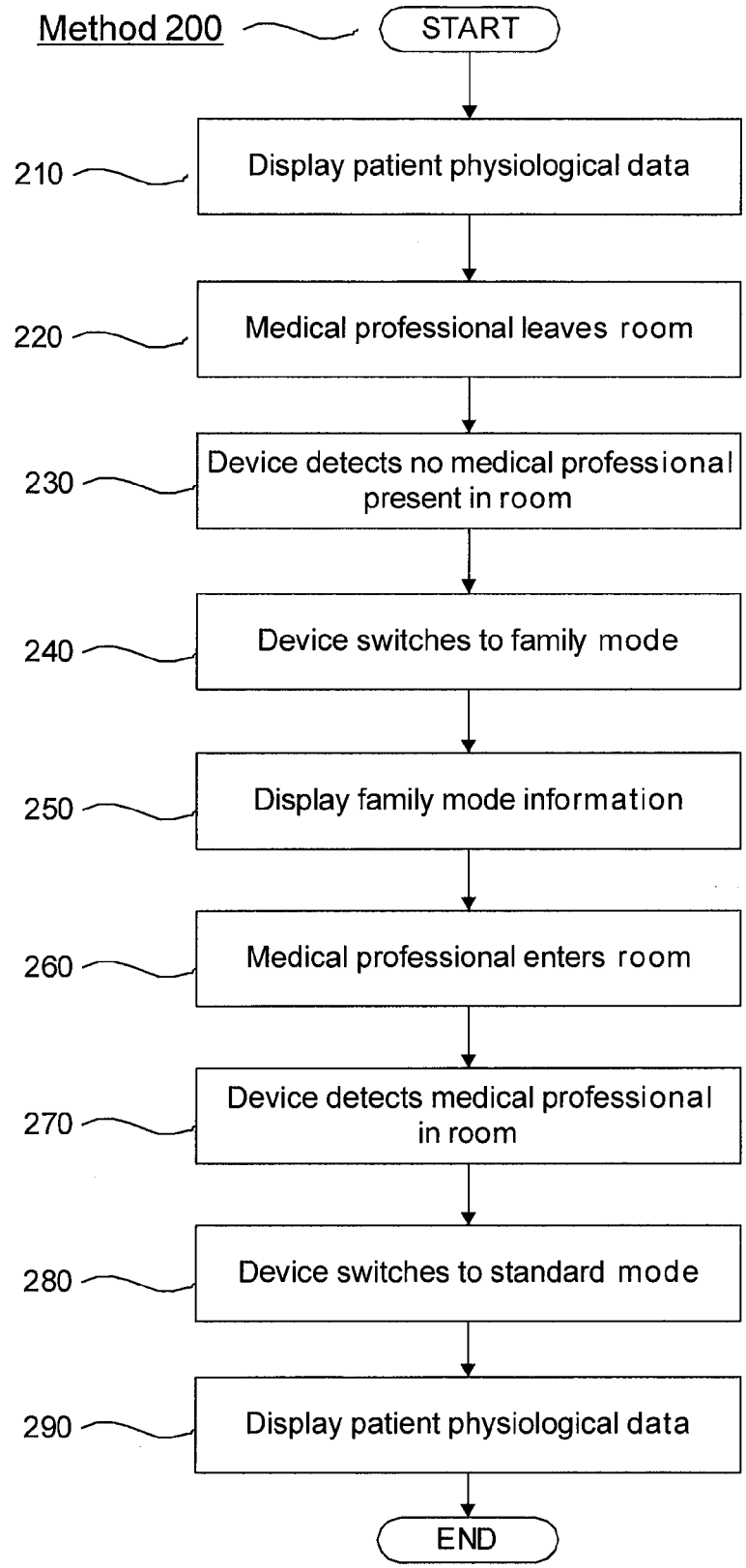
FIG. 2 illustrates an exemplary method for providing a family mode for patient monitoring devices.

FIG. 2 illustrates an exemplary method 200 for providing family mode on a patient monitoring device such as the patient monitoring device 130 described above. The method 200 will be described specifically with reference to the elements of the system 100, but those of skill in the art will understand that other combinations of physical elements may also be operative to perform the exemplary method 200. At the commencement of the method 200, a medical professional is in the patient's room. In step 210, the patient monitoring device displays physiological data for the patient 100 using the display 133. As described above, the physiological data to be displayed may include ECG data, respiratory rate, heart rate, oxygen saturation, blood pressure, or various other data. In step 220, the medical professional leaves the patient's room. In step 230, the medical professional detection element 140 detects that no medical professional is present in the room; as described above, this may be accomplished by detecting no medical professional's identification badge within proximity to the medical professional detection element 140, an operation of a physical switching device, receipt of a voice command, etc.

In step 240, the patient monitoring device 130 switches to family mode in response to the detection of step 230, and in step 250 the patient monitoring device 130 displays family mode information. While in family mode, the display 133 shows information that is appropriate for the patient 100 and the patient's family and friends, rather than the physiological data described above. Various types of information are possible, and differing implementations may include one, some, or all of the types of information to be described below, or other types of information not described herein. In a first example, the display 133 shows some or all of the physiological data described above, but the data is provided in a manner that is appropriate for a lay viewer.

In a second example, the display 133 shows some or all of the physiological patient data described above, together with educational information informing the patient 100 what the data shown measure, why the measured data is important, and what the expected values are. The educational information may include text, graphics, video, etc. If an alarm is triggered by the patient's information, the display 133 may also provide information about what the alarm indicates. In a third example, the display 133 shows educational information about the patient's condition, information about the patient's medication (e.g., in one embodiment the display 133 prompts the patient 100 to take medication when appropriate), information to prepare the patient for eventual discharge, etc. In a fourth example, the display 133 shows a list of the patient's care providers. The list may be categorized by the type of care or in another manner, and may include specifics about the care providers' roles and contact information.

In a fifth example, the display 133 shows calendar or schedule information. This may include events that are specific to the patient 100 and family (e.g., the day and time of a cancer patient's next radiotherapy treatment, the day and time when a surgery is scheduled for the patient, etc.), events of general interest to all patients and their families (e.g., the time and location of religious services offered in a hospital, etc.), or both. In a sixth example, the display 133 may operate as a digital photo frame displaying photos provided by the patient 100. Photos to be displayed in this manner may be stored in the memory 132, stored in a portable memory (e.g., a USB memory, an SD memory card, etc.) connected to the patient monitoring device 130, streamed from an online source via the network data interface 136, etc.

In one exemplary embodiment, while in family mode the patient monitoring device 130 may categorize alerts based on the patient physiological data into low-level alerts and high-level alerts. When a high-level alert occurs, the alert is activated both at the patient monitoring device 130 and at a remote monitoring station. Conversely, when a low-level alert is occurred, the alert is activated only at a remote monitoring station, in order to avoid unnecessarily alarming the patient or the patient's family about minor issues. In another exemplary embodiment, family mode may include a night mode to be active during night hours. (The specific hours during which night mode is active may be configured by the patient, the patient's doctor, etc., and may also vary depending on the nature of the patient's condition.) During night mode, the display 133 may be blank or may display minimal information in a manner that minimizes the brightness of the patient's room, and audio alerts may be silenced or provided at a lower volume.

In a further exemplary embodiment, a patient monitoring device 130 that is located in a hospital room can be controlled by the same remote control that is used to control the TV set that is typically also present in a hospital room. In this embodiment, the patient monitoring device 130 includes additional hardware (e.g., an IR detection port) to detect signals emitted by the remote control. In such an embodiment, the patient 110 or the patient's family can use the remote control, for example, to switch between a mode in which the display 133 shows educational information about the patient's condition and a mode in which the display 133 shows schedule information; however, the remote control is not operative to control the patient monitoring device 130 when the patient monitoring device 130 is in its standard mode displaying patient physiological data, as described above with reference to step 210.

Returning to the method 200, in step 260 a medical professional enters the patient's room. Those of skill in the art will understand that this may occur in response to a patient request (e.g., the use of a "call" button), as a scheduled visit, in response to an alarm generated by the patient monitoring device 130, or for any of the other various reasons known in the art. In step 270, the medical professional detection element 140 detects that the medical professional has entered the room; as described above, this may be accomplished automatically, such as through the detection of an identification badge containing an RFID chip, or manually, such as through the use of a switch or voice recognition. In step 280, in response to the detection of step 270, the patient monitoring device 130 switches from the family mode described above to the standard mode that is known in the art. Last, in step 290, the display 133 displays patient physiological data, as described above with reference to step 210.

The exemplary embodiments described above enable medical professionals to be provided with all patient physiological information that is typically provided by a device such as the patient monitoring device 130. Further, the availability of family mode, as described above, enables devices such as the patient monitoring device 130 to provide information that is appropriate for lay observers to patients and their families, in order to educate them about the patient's condition and provide various other useful information without providing information that may be confusing or misleading. Additionally the exemplary embodiments may typically be implemented with hardware that is substantially similar to that of patient monitoring devices that do not include a family mode option, except where described above.

Those skilled in the art will understand that the above-described exemplary embodiments may be implemented in any number of manners, including, as a separate software module, as a combination of hardware and software, etc. For example, the method 200 may be a program containing lines of code that, when compiled, may be executed on a processor. Further, those skilled in the art will understand that while the exemplary embodiments are described specifically with reference to a patient monitoring device as described above, the broader principles so embodied may be equally applicable to other patient devices having always-on displays such as ventilators, IV pumps, etc.

It is noted that the claims may include reference signs/numerals in accordance with PCT Rule 6.2(b). However, the present claims should not be considered to be limited to the exemplary embodiments corresponding to the reference signs/numerals.

It will be apparent to those skilled in the art that various modifications may be made in the present invention, without departing from the spirit or the scope of the invention. Thus, it is intended that the present invention cover modifications and variations of this invention provided they come within the scope of the appended claims and their equivalents.

What is claimed is:

1. A non-transitory computer-readable storage medium storing a set of instructions executable by a processor, the set of instructions being operable to:
   receive patient physiological data;
   receive an indication indicating whether a medical professional is present in a patient's room;
   display, on a display of a patient monitoring device, a first display mode, if a medical professional is present in the patient's room, the first display mode including the patient physiological data;
   display, on the display of the patient monitoring device, a second display mode, if a medical professional is not present in the patient's room, the second display mode being adapted for viewing by lay viewers, wherein the second display mode includes one of a simplified version of patient physiological data, an educational display about a patient's condition, a list of care providers, a calendar, and a photograph;
   generate an alert in response to the patient physiological data;
   categorize the alert as a high-level alert or a low-level alert based on the patient physiological data;
   generate an alarm in the patient's room and at a remote monitoring location, if the alert is a high-level alert; and
   generate an alarm at the remote monitoring location and not in the patient's room, if the alert is a low-level alert.

2. The non-transitory computer-readable storage medium of claim 1, wherein receiving the indication comprises one of detecting a badge worn by a medical professional and receiving an input from a medical professional.

3. The non-transitory computer readable storage medium of claim 2, receiving the indication comprises detecting a badge worn by a medical professional, and wherein the badge uses one of active technology and passive technology.

4. The non-transitory computer-readable storage medium of claim 1, wherein the patient physiological data includes one of an ECG, a respiratory rate, a heart rate, an oxygen saturation, and a blood pressure.

5. The non-transitory computer-readable storage medium of claim 1, wherein the set of instructions is further operable to:
transmit the patient physiological data to a remote monitoring station.

6. The non-transitory computer-readable storage medium of claim 1, wherein the second display mode includes a plurality of the simplified version of the patient physiological data, the educational display about a patient's condition, the list of care providers, the calendar, and the photograph, and wherein the set of instructions is further operable to:
receive a selection of one of one of the simplified version of the patient physiological data, the educational display about a patient's condition, the list of care providers, the calendar, and the photograph; and
display the selected one of the simplified version of the patient physiological data, the educational display about a patient's condition, the list of care providers, the calendar, and the photograph.

7. The non-transitory computer-readable storage medium of claim 6, wherein the selection is received from a remote control that is further operable to control a television.

8. The non-transitory computer-readable storage medium of claim 1, wherein when the second display mode is displayed, the display is darkened at night.

9. A device, comprising:
a sensor detecting patient physiological data;
a detection element detecting whether a medical professional is present in a patient's room; and
a display;
wherein, if a medical professional is present in the patient's room, the display displays a first display mode, the first display mode including the patient physiological data, and wherein, if a medical professional is not present in the patient's room, the display displays a second display mode, the second display mode being adapted for viewing by lay viewers, wherein the second display mode includes one of a simplified version of patient physiological data, an educational display about a patient's condition, a list of care providers, a calendar, and a photograph;
a processor configured to generate an alert in response to the patient physiological data, categorize the alert as a high-level alert or a low-level alert based on the patient physiological data, generate an alarm in the patient's room and at a remote monitoring location, when the alert is a high-level alert and generate an alarm at the remote monitoring location and not in the patient's room, when the alert is a low-level alert.

10. The device of claim 9, wherein the detection element detects whether a medical professional is present in the patient's room by one of:
detecting a badge worn by a medical professional, and
receiving input from a medical professional.

11. The device of claim 10, wherein the detection element detects whether a medical professional is present in the patient's room by detecting a badge worn by a medical professional, and wherein the badge uses one of active technology and passive technology.

12. The device of claim 9, wherein the patient physiological data includes one of an ECG, a respiratory rate, a heart rate, an oxygen saturation, and a blood pressure.

13. The device of claim 9, further comprising:
A data interface transmitting the patient physiological data to a remote monitoring station.

14. The device of claim 9, wherein the second display mode includes a plurality of the simplified version of the patient physiological data, the educational display about a patient's condition, the list of care providers, the calendar, and the photograph, and wherein the system receives a selection of one of one of the simplified version of the patient physiological data, the educational display about a patient's condition, the list of care providers, the calendar, and the photograph, and displays the selected one of the simplified version of the patient physiological data, the educational display about a patient's condition, the list of care providers, the calendar, and the photograph.

15. The device of claim 14, wherein the selection is received from a remote control that is further operable to control a television.

16. The device of claim 9, wherein when the second display mode is displayed, the display is darkened at night.

* * * * *